United States Patent
Bosch et al.

(10) Patent No.: US 12,347,901 B2
(45) Date of Patent: Jul. 1, 2025

(54) DEVICE FOR DETERMINING THE HYDROGEN CONCENTRATION OF AN EXHAUST GAS IN AN EXHAUST GAS LINE OF A FUEL CELL SYSTEM, AND FUEL CELL SYSTEM

(71) Applicant: Robert Bosch GmbH, Stuttgart (DE)

(72) Inventors: Timo Bosch, Renningen (DE); Tobias Falkenau, Esslingen (DE)

(73) Assignee: Robert Bosch GmbH, Stuttgart (DE)

( * ) Notice: Subject to any disclaimer, the term of this patent is extended or adjusted under 35 U.S.C. 154(b) by 322 days.

(21) Appl. No.: 18/028,035

(22) PCT Filed: Sep. 22, 2021

(86) PCT No.: PCT/EP2021/076042
§ 371 (c)(1),
(2) Date: Mar. 23, 2023

(87) PCT Pub. No.: WO2022/063813
PCT Pub. Date: Mar. 31, 2022

(65) Prior Publication Data
US 2023/0343975 A1    Oct. 26, 2023

(30) Foreign Application Priority Data
Sep. 25, 2020   (DE) .................. 10 2020 212 109.5

(51) Int. Cl.
*H01M 8/0444* (2016.01)
*G01N 33/00* (2006.01)
*H01M 8/04089* (2016.01)

(52) U.S. Cl.
CPC ...... *H01M 8/04462* (2013.01); *G01N 33/005* (2013.01); *H01M 8/04097* (2013.01); *H01M 8/0447* (2013.01)

(58) Field of Classification Search
None
See application file for complete search history.

(56) References Cited

U.S. PATENT DOCUMENTS

| | | |
|---|---|---|
| 6,455,181 B1 | 9/2002 | Hallum |
| 2007/0026275 A1 | 2/2007 | Sasaki et al. |

FOREIGN PATENT DOCUMENTS

| | | |
|---|---|---|
| CN | 109768307 A | 5/2019 |
| DE | 102009052473 A1 | 5/2011 |

(Continued)

OTHER PUBLICATIONS

Translation of International Search Report for Application No. PCT/EP2021/076042 dated Jan. 12, 2022 (2 pages).

*Primary Examiner* — Daniel S Larkin
(74) *Attorney, Agent, or Firm* — Michael Best & Friedrich LLP

(57) ABSTRACT

A device (1) for determining the H2 concentration of a fluid in an exhaust gas line (12) of a fuel cell system (100) includes a sensor (14) arranged in a pipe section (2), and the pipe section has an inflow opening (4) and an outflow opening (6). An installation element (8) divides exhaust gas arriving through the inflow opening (4) into a first volumetric flow which flows through a first pipe volume (V1) and at least one additional volumetric flow which flows through at least one additional pipe volume (V2). A purge line (41) opens into the first pipe volume (V1) between the inflow opening (4) and the H2 sensor (14). The sensor (14) measures the H2 concentration of the exhaust gas in the first pipe volume (V1).

10 Claims, 5 Drawing Sheets

(56) References Cited

FOREIGN PATENT DOCUMENTS

| | | | |
|---|---|---|---|
| JP | 2001165739 | A | 6/2001 |
| JP | 2003329631 | A | 11/2003 |
| JP | 2006012715 | A | 1/2006 |
| JP | 2006017619 | A | 1/2006 |
| JP | 2007040756 | A | 2/2007 |
| JP | 2010182458 | A | 8/2010 |
| JP | 2013032987 | A | 2/2013 |
| JP | 5190561 | B2 | 4/2013 |
| WO | 2020181751 | A1 | 9/2020 |

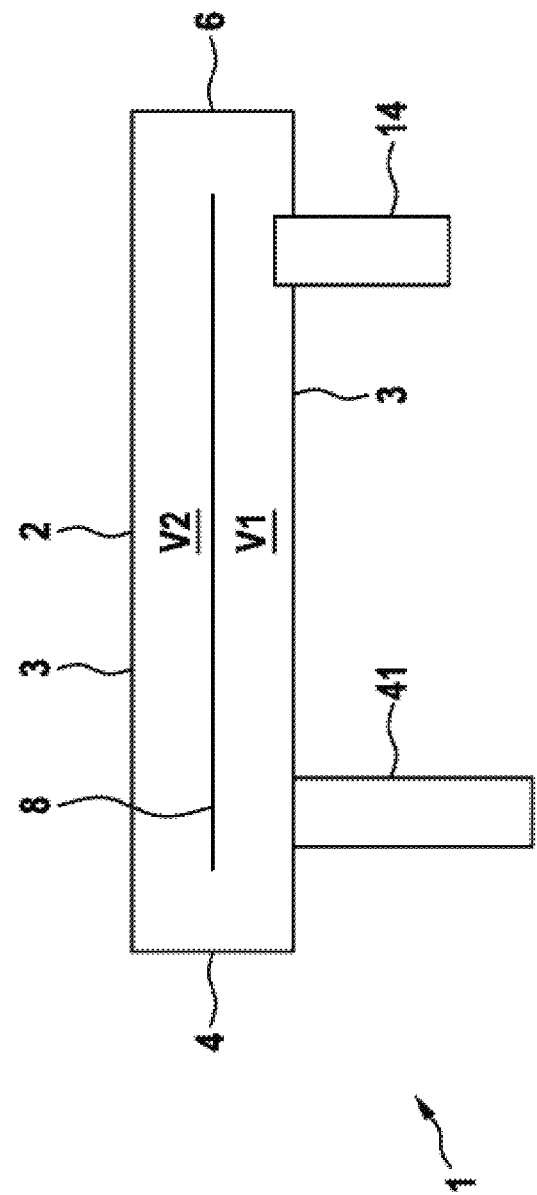

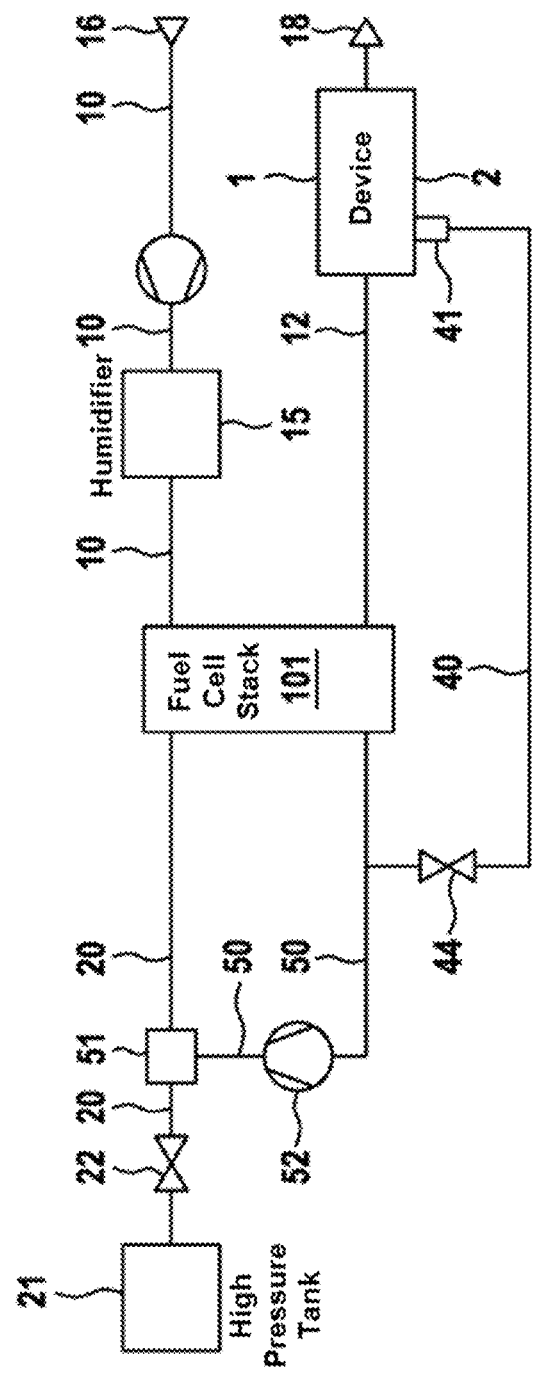

DEVICE FOR DETERMINING THE HYDROGEN CONCENTRATION OF AN EXHAUST GAS IN AN EXHAUST GAS LINE OF A FUEL CELL SYSTEM, AND FUEL CELL SYSTEM

BACKGROUND

The present application is a national stage entry of International Patent Application No. PCT/EP2021/076042, filed Sep. 22, 2021, which claims priority to German Patent Application No. DE102020212109A, filed Sep. 25, 2020.

The invention relates to a device for determining the hydrogen concentration of an exhaust gas in an exhaust gas line of a fuel cell system. The invention also relates to a fuel cell system.

Hydrogen-based fuel cells are considered to be the mobility concept of the future since they emit only water as exhaust gas and allow fast refueling times. Fuel cells are usually assembled into a fuel cell stack. The fuel cell stacks use oxygen, mostly obtained from simple air from the environment, and fuel, mostly hydrogen, for the chemical reaction.

It is known that nitrogen reaches the cathode side of the fuel cell stack via the air mass flow, which is supplied to the fuel cell stack via the air path. Part of this nitrogen diffuses across the membrane of the fuel cell stack to the anode side and displaces the hydrogen on the anode side, so that the normal reactions are inhibited. To reduce the proportion of nitrogen on the anode side, a valve with a flushing line can lead from the anode side, or from the circulation line, to the exhaust gas line of the fuel cell to discharge anode gas with a proportion of nitrogen to the environment via the exhaust gas line. To check the proportion of hydrogen in the exhaust gas line, a hydrogen sensor is disposed in the exhaust gas line.

It is also known that hydrogen passes from the anode side to the cathode side. Some of this hydrogen is burned catalytically and some of it enters the cathode exhaust gas with the enriched cathode air.

SUMMARY

The device according to the invention for determining the hydrogen concentration of an exhaust gas in an exhaust gas line of a fuel cell system and the fuel cell system having the features according to the independent claims has the advantage that the hydrogen content in the exhaust gas line can be determined with greater accuracy. This is important so that, if necessary, measures can be taken to avoid an excessively high concentration of hydrogen and thus an explosive mixture.

Without the device according to the invention, there is a risk that the sensor will detect too low or too high a concentration of hydrogen in the exhaust gas, because the measurement accuracy of the measuring means decreases disproportionately when measuring low proportions.

The device according to the invention furthermore makes it possible to better differentiate the introduction of hydrogen from the anode from particularly low concentrations from the cathode. An increase in this value can thus be used to infer the presence of holes in the membrane, for example.

From an economic point of view, the device according to the invention can be used to reduce the accuracy requirement on the sensor while maintaining the measurement accuracy, thus saving costs.

The protection against liquid water by the device according to the invention is furthermore advantageous for the reliability and the service life of the sensor.

One way to counteract an excessively high concentration of hydrogen is to interrupt the supply of hydrogen from the anode side by purging and draining. Another way is to selectively increase the air mass flow in the exhaust gas line, which can potentially be fed directly from the air path into the exhaust gas line via a bypass connector. Another option is to catalytically burn the hydrogen.

Advantageous embodiments and further developments of the device according to the invention for determining the hydrogen concentration of an exhaust gas in an exhaust gas line of a fuel cell system and the fuel cell system are specified in the dependent claims.

It is advantageous if the pipe section comprises a connector for a purge line, since a purge gas of the purge line is fed into the first volume via the connector, so that the concentration of hydrogen in the purge gas can be determined with high accuracy.

To ensure that the purge gas from the purge line and the exhaust gas from the exhaust gas line are mixed as uniformly as possible, it is advantageous if a swirl element 75 is disposed between the connector and the sensor.

It is advantageous if the installation element is formed by at least one rectangular plate, because this is a simple and cost-efficient solution for directing the flow past the sensor in a targeted manner.

It is advantageous if the installation element is configured as a pipe element, because this form of the installation element makes it easier to realize a measurement in the center of the pipe section.

It is advantageous if the pipe element is fixed inside the pipe section via the connector and/or a mount of the sensor, since no additional mounts are required, so that costs can be saved.

Depending on the local flow conditions, the installation element makes it possible to fix the sensor to an outer wall of the pipe section or to the installation element as needed.

BRIEF DESCRIPTION OF THE DRAWINGS

The device according to the invention and the fuel cell system according to the invention are explained in more detail in the following with reference to drawings. Schematically, the figures show:

FIG. 2 illustrates a device for determining the H2 concentration of a fluid in an exhaust gas line of a fuel cell system in a schematic illustration, FIG. 3 is a schematic topology of a fuel cell system according to a second embodiment example of the invention.

DETAILED DESCRIPTION

Figure 1:
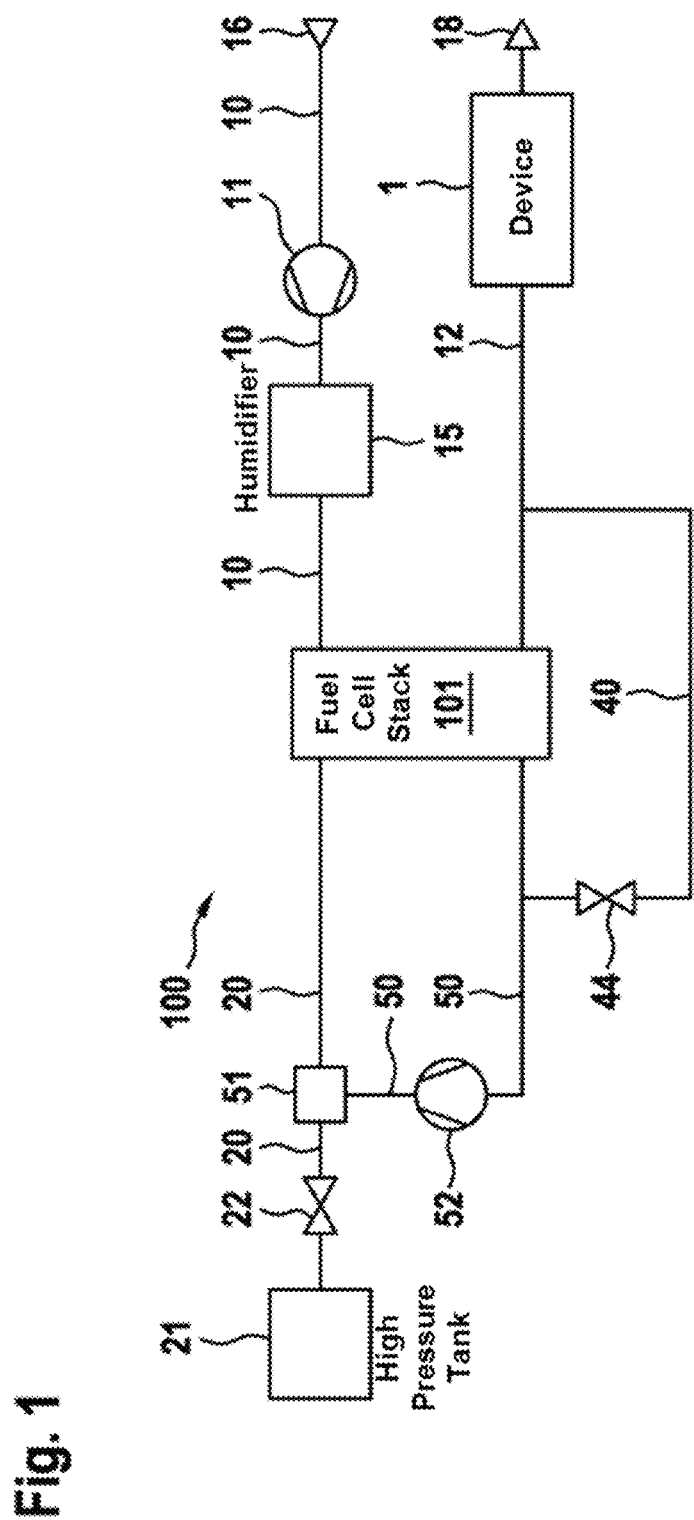
FIG. 1 is a schematic topology of a fuel cell system according to a first embodiment example of the invention.

FIG. 1 shows a schematic topology of a fuel cell system 100 according to a first embodiment example with at least one fuel cell stack 101. The at least one fuel cell stack 101 comprises an air path 10, an exhaust gas line 12 and a fuel line 20. The at least one fuel cell stack 101 can be used for mobile applications with a high power requirement, for example in trucks, or for stationary applications, for example in generators.

The air path 10 serves as an air supply line for supplying air from the environment to the at least one fuel cell stack 101 via an inlet 16. Components needed for the operation of the at least one fuel cell stack 101 are disposed in the air path 10. An air compressor 11 and/or compressor 11, which compresses and/or draws in the air in accordance with the respective operating conditions of the at least one fuel cell stack 101, is disposed in the air path 10. A humidifier 15 which enriches the air in the air path 10 with a higher concentration of liquid can be disposed downstream of the air compressor 11 and/or compressor 11.

Further components, such as a filter and/or a heat exchanger and/or valves, can be provided in the air path 10 as well. Air containing oxygen is made available to the at least one fuel cell stack 101 via the air path 10.

The fuel cell system 100 also comprises an exhaust gas line 12 in which water and other components of the air from the air path 10 are transported into the environment via an outlet 18 after passing through the at least one fuel cell stack 101. The exhaust gas of exhaust gas line 12 can also contain hydrogen (H2), because portions of the hydrogen can diffuse through the membrane of the fuel cell stack 101.

The fuel cell system 100 can moreover comprise a cooling circuit configured to cool the at least one fuel cell stack 101. The cooling circuit is not shown in FIG. 1 because it is not part of the invention.

A high pressure tank 21 and a shut-off valve 22 are disposed in the inlet of fuel line 20. Additional components can be disposed in the fuel line 20 to supply fuel to the at least one fuel cell stack 101 as needed.

To always adequately supply the fuel cell stack 101 with fuel, there is a need for an overstoichiometric metering of fuel via the fuel line 20. The excess fuel, and also certain amounts of water and nitrogen that diffuse through the cell membranes to the anode side, are recirculated in a recirculation line 50 and mixed with the metered fuel from the fuel line 20.

Various components, such as a jet pump 51 operated with the metered fuel or a blower 52, can be installed to drive the recirculation line 50. A combination of jet pump 51 and blower 52 are possible as well.

Since the amount of water and nitrogen increases more and more over time, the recirculation line 50 has to be flushed periodically so that the performance of the at least one fuel cell stack 101 does not decrease due to an excessive concentration of nitrogen in the fuel line 20.

A purge line 40 is disposed between the recirculation line 50 and the exhaust gas line 12 so that the gas mixture can flow from the recirculation line 50 into the exhaust gas line 12.

A purge valve 44 which can open and close the connection between the recirculation line 50 and the exhaust gas line 12 can be disposed in the purge line 40. The purge valve 44 is typically opened for a short period of time, so that the gas mixture is fed into the exhaust gas line 12 via the purge line 40.

According to one embodiment of the invention, a device 1 for determining the H2 concentration is disposed in the exhaust gas line 12.

FIG. 2 shows a device 1 for determining the H2 concentration in a schematic illustration. The device 1 is formed by a pipe section 2 comprising a sensor 14, which can measure the hydrogen concentration in a fluid. The pipe section 2 comprises an inflow opening 4 and an outflow opening 6. Also disposed in the pipe section 2 is an installation element 8 which divides the exhaust gas that has passed through the inflow opening 4 into a first volumetric flow that flows through a first pipe volume V1 and a second volumetric flow that flows through a second pipe volume V2.

In a further embodiment of the invention, the pipe section 2 can comprise a connector 41 for the purge line 40. The connector 41 establishes a connection between the first volume V1 and the purge line 40. The purge gas of the purge line 40 is directed through the connector 41 into the first volume V1.

The connector 41 for the purge line 40 is disposed between the inflow opening 4 and the sensor 14, so that, when measuring, the sensor 14 measures the H2 concentration from both the exhaust gas line 12 and the purge line 40.

FIG. 1 shows a fuel cell system 100 comprising a device without a connector 41, in which the purge line 40 opens into the exhaust gas line 12 in front of the device 1 in the direction of flow.

FIG. 3 shows a fuel cell system 100 comprising a device 1 with a connector 41. Here the purge line 40 is connected to the connector 41, so that the purge gas can flow directly from the purge line 40 via the connector 41 into the first volume V1 of the pipe section 2.

In order to achieve the best possible mixing of the exhaust gas from the exhaust gas line 12 and the purge gas from the purge line 40, a swirl element 75 can be disposed in the first pipe volume V1 between the connector 41 and the sensor 14.

FIG. 4 shows a cross-section through three devices 1 comprising different installation elements 8, which are each formed by at least one rectangular plate.

Figure 4A:
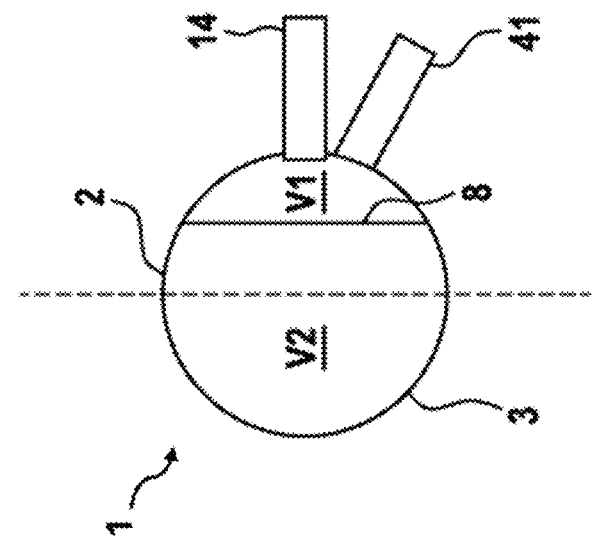
FIGS. 4a-4c illustrate devices for determining the H2 concentration of a fluid in an exhaust gas line of a fuel cell system with different installation elements in a schematic illustration and FIGS. 5a-5b illustrate a device for determining the H2 concentration of a fluid in an exhaust gas line of a fuel cell system with an installation element configured as a pipe in a schematic illustration.

In FIG. 4a, a rectangular sheet is disposed parallel to a perpendicular bisector (indicated by the dashed line) of the pipe section 2, so that a smaller first pipe volume V1 and a larger second pipe volume V2 are formed.

Figure 4B:
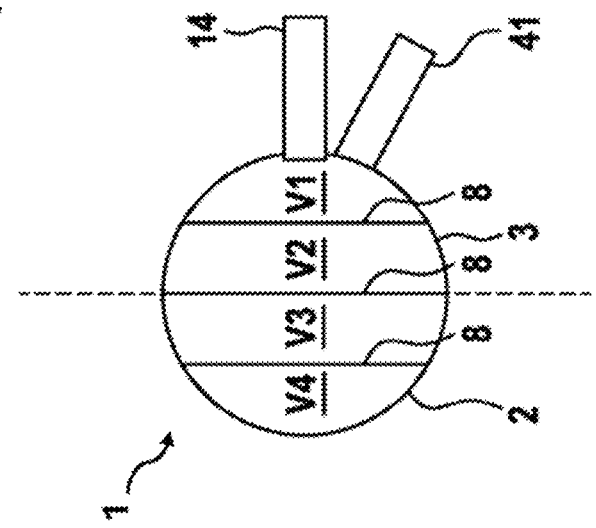

In FIG. 4b, three rectangular plates 8 are disposed parallel to a perpendicular bisector (indicated by the dashed line) of the pipe section 2, so that four pipe volumes V1, V2, V3 and V4 are formed.

Figure 4C:
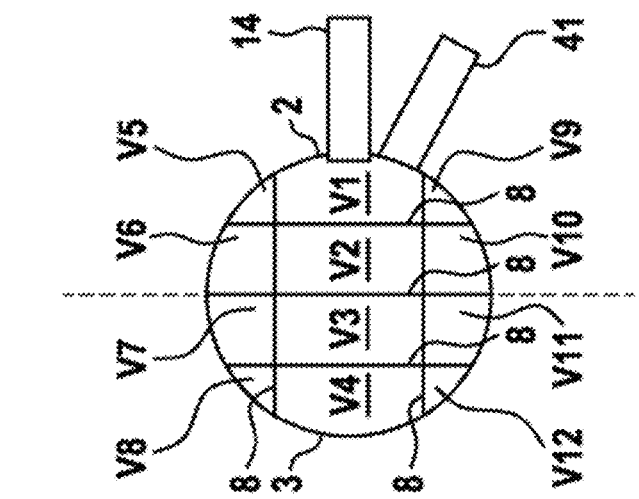

In FIG. 4c, three rectangular plates 8 are disposed parallel to a perpendicular bisector (indicated by the dashed line) of the pipe section 2 and two rectangular plates have additionally been disposed perpendicular to the perpendicular bisector, so that twelve pipe volumes V1, V2, V3, . . . , V12 are formed.

Figure 5B:
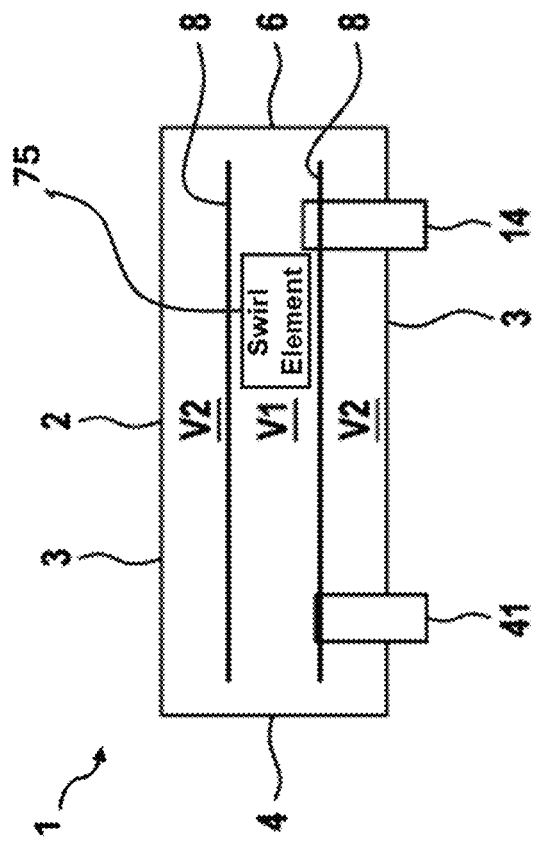
Figure 5A:
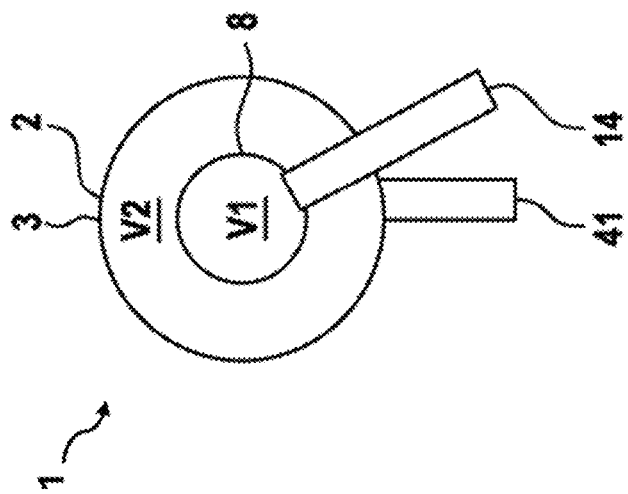

FIG. 5 shows an embodiment of the device 1 in which the installation element 8 is formed by a pipe element. FIG. 5a shows a cross-section through the device 1, in which the sectional plane has been selected perpendicular to the main flow direction. FIG. 5b shows a cross-section through the device 1, in which the sectional plane has been selected parallel to the main flow direction.

In the shown embodiment example, the installation element 8 is a circular pipe element, which is disposed in the pipe volume in such a way that two concentric circles are formed in the sectional plane. The first pipe volume V1 can be selected inside the pipe element 8, as shown.

The pipe element 8 has no direct contact with the outer wall 3 of the pipe section 2 and is fixed inside the pipe section 2 via the connector 41 and/or a mount of the sensor 14.

The sensor 14 can be attached to an outer wall 3 of the pipe section 2 or to the installation element 8, depending on the selection of the first pipe volume V1. The sensor can also be attached to the outer wall 3, so that measurements are carried out in the volume V2.

What is claimed is:

1. A device (1) configured for determining the hydrogen concentration of an exhaust gas in an exhaust gas line (12) of a fuel cell system (100), comprising a sensor (14), which is disposed in a pipe section (2), wherein the pipe section (2) comprises an inflow opening (4) and an outflow opening (6), wherein an installation element (8) divides the exhaust gas which has passed through the inflow opening (4) into a first volumetric flow which flows through a first pipe volume (V1) and at least one further volumetric flow which flows through at least one further pipe volume (V2), wherein the sensor (14) measures the hydrogen concentration of the exhaust gas in the first pipe volume (V1), wherein the pipe section (2) comprises a connector (41) configured for a purge line (40), wherein a purge gas from the purge line (40) is fed into the first pipe volume (V1) via the connector (41).

2. The device (1) according to claim 1, wherein the connector (41) configured for the purge line (40) is disposed between the inflow opening (4) and the sensor (14).

3. The device (1) according to claim 2, wherein a swirl element (75) is disposed between the connector (41) and the sensor (14).

4. The device (1) according to claim 1, wherein the installation element (8) is formed by at least one rectangular plate.

5. The device (1) according to claim 1, wherein the installation element (8) is a pipe element.

6. The device (1) according to claim 5, wherein the pipe element (8) has no direct contact with an outer wall (3) of the pipe section (2) and is fixed inside the pipe section (2) via a connector (41) and/or a mount of the sensor (14).

7. The device (1) according to claim 1, wherein the sensor (14) is fixed to an outer wall (3) of the pipe section (2) or to the installation element (8).

8. A fuel cell system (100) comprising at least one fuel cell stack (101), an air path (10), wherein air from environment reaches the at least one fuel cell stack via the air path (10), an exhaust gas line (12), a fuel line (20), wherein fuel is transported to the at least one fuel cell stack (101) via the fuel line (20), and a circulation line (50), wherein the recirculation line (50) comprises a purge line (40), wherein a device (1) according to claim 1 is disposed in the exhaust gas line (12).

9. The fuel cell system (100) according to claim 8, wherein the purge line (40) is connected to a connector (41) of the device (1).

10. A device (1) configured for determining the hydrogen concentration of an exhaust gas in an exhaust gas line (12) of a fuel cell system (100), comprising a sensor (14), which is disposed in a pipe section (2), wherein the pipe section (2) comprises an inflow opening (4) and an outflow opening (6), wherein an installation element (8) divides the exhaust gas which has passed through the inflow opening (4) into a first volumetric flow which flows through a first pipe volume (V1) and at least one further volumetric flow which flows through at least one further pipe volume (V2), wherein the sensor (14) measures the hydrogen concentration of the exhaust gas in the first pipe volume (V1), wherein the installation element (8) is a pipe element, wherein the pipe element has no direct contact with an outer wall (3) of the pipe section (2) and is fixed inside the pipe section (2) via a connector (41) and/or a mount of the sensor (14).

* * * * *